United States Patent [19]

Jaen et al.

[11] Patent Number: 5,187,280
[45] Date of Patent: Feb. 16, 1993

[54] SUBSTITUTED TETRAHYDROPYRIDINES AND THEIR USE AS CENTRAL NERVOUS SYSTEM AGENTS

[75] Inventors: Juan C. Jaen, Plymouth; David G. Nickell, Ann Arbor; Donna M. Reynolds, Plymouth; Sarah J. Smith, Ann Arbor; Lawrence D. Wise, Ann Arbor; David J. Wustrow, Ann Arbor, all of Mich.

[73] Assignee: Warner-Lambert Company, Morris Plains, N.J.

[21] Appl. No.: 746,434

[22] Filed: Aug. 16, 1991

Related U.S. Application Data

[62] Division of Ser. No. 585,758, Sep. 20, 1990, Pat. No. 5,045,550.

[51] Int. Cl.$^5$ .................. C07D 401/14; C07D 405/14; C07D 417/14; A61K 31/44

[52] U.S. Cl. .................. 546/255; 546/257; 546/255

[58] Field of Search .............. 546/255, 256; 514/332, 514/333, 257

[56] References Cited

U.S. PATENT DOCUMENTS 4,665,187  5/1987  Bottcher ........................ 544/255

Primary Examiner—David B. Springer
Attorney, Agent, or Firm—Francis J. Tinney

[57] ABSTRACT

Substituted tetrahydropyridines and derivatives thereof are described, as well as methods for the preparation and pharmaceutical composition of same, which are useful as central nervous system agents and are particularly useful as dopaminergic, antipsychotic, and antihypertensive agents as well as for treating hyperprolactinaemia-related conditions and central nervous system disorders.

6 Claims, No Drawings

SUBSTITUTED TETRAHYDROPYRIDINES AND THEIR USE AS CENTRAL NERVOUS SYSTEM AGENTS

This is a divisional application of U.S. Ser. No. 07/585,758 filed Sep. 20, 1990, now U.S. Pat. No. 5,045,550.

BACKGROUND OF THE INVENTION

The present invention relates to novel substituted tetrahydropyridines and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

A series of pyridine derivatives of the formula

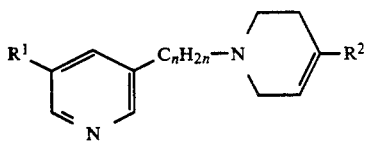

wherein $R^1$ and $R^2$ are independently each phenyl or 2-or 3-thienyl radicals which are unsubstituted or monosubstituted or disubstituted by alkyl, alkoxy, F, Cl, Br, OH, and/or $CF_3$ and n is 1, 2, or 3, and the alkyl and alkoxy groups each have 1–4 C atoms and salts thereof having suppressant actions on the central nervous system is disclosed in U.S. Pat. No. 4,665,187.

However, the compounds disclosed in the aforementioned references do not disclose or suggest the combination of structural variations of the compounds of the present invention described hereinafter.

SUMMARY OF THE INVENTION

Accordingly, the present invention is a compound of Formula I

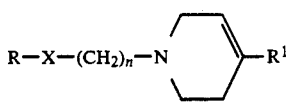

wherein
R is

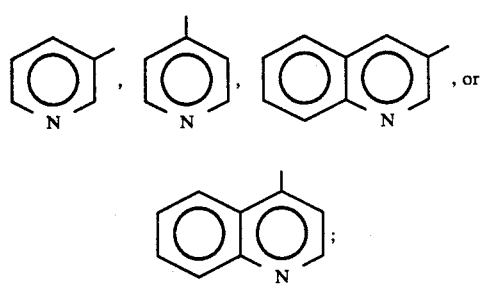

X is $$-\overset{\overset{\displaystyle O}{\|}}{C}-,$$

or $-CH_2-$;

n is an integer of 2 to 4;

$R^1$ is aryl, 2- or 3-1H-indolyl, or 2- or -1H-indolyl substituted by lower alkyl, lower alkoxy, or halogen, 2-, 3-, or 4-pyridinyl, or 2-, 3-, or -pyridinyl substituted by lower alkyl, lower alkoxy, or halogen, 2-, 4-, or 5-pyrimidinyl, or 2-, 4-, or -pyrimidinyl substituted by lower alkyl, lower alkoxy, or halogen, 2-pyrazinyl or 2-pyrazinyl substituted by lower alkyl, lower alkoxy, or halogen, 2- or 3-thienyl, or 2- or 3-thienyl substituted by lower alkyl or halogen, 2- or 3-furanyl, or 2- or 3-furanyl substituted by lower alkyl or halogen, 2-, 4-, or 5-thiazolyl, or 2-, 4-, or 5-thiazolyl substituted by lower alkyl or halogen; or a pharmaceutically acceptable acid addition salt thereof.

As dopaminergic agents, the compounds of Formula I are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to four substituents selected from lower alkyl, lower alkoxy, lower thioalkoxy, halogen or trifluoromethyl such as, for example, benzyl, phenethyl, and the like.

"Lower alkoxy" and "thioalkoxy" are 0-alkyl or S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

"Noble metal" is platinum, palladium, rhodium, ruthenium, and the like.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal Pharmaceutical Science*, Vol. 66. pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I is one wherein $R^1$ is aryl, 2- or 3-1H-indolyl, or 2- or 3-1H-indolyl substituted by lower alkyl, lower alkoxy, or halogen, 2-, 3-, or 4 pyridinyl or 2-, 3-, or 4 pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2- or 3-thienyl or 2- or 3-thienyl substituted by lower alkyl or halogen.

Another preferred embodiment is a compound of Formula I wherein $R^1$ is aryl, 2- or 3-1H-indolyl, 2-, 3-, or 4-pyridinyl, 2-, 4-, or 5-pyrimidinyl, or 2- or 3-thienyl.

Particularly valuable are:
4-(3,6-Dihydro-4-phenyl-1(2H)-pyridinyl)-1-(3-pyridinyl)-1-butanone;
3-[4-(3,6-Dihydro-4-phenyl-1(2H)-pyridinyl)-butyl]-pyridine;
3-[4-[3,6-Dihydro-4-(2-thienyl)-1(2H)-pyridinyl]-butyl]-pyridine;
4-(3,6-Dihydro-4-phenyl-1(2H)-pyridinyl)-1-(4-pyridinyl)-1-butanone;
4-[4-(3,6-Dihydro-4-phenyl-1(2H)-pyridinyl)-butyl]-pyridine;
2-[1,2,3,6-Tetrahydro-1-[4-(4-pyridinyl)butyl]-4-pyridinyl]pyridine;
3-[1,2,3,6-Tetrahydro-1-[4-(4-pyridinyl)butyl]-4-pyridinyl]-1H-indole;
4-[4-[3,6-Dihydro-4-(2-thienyl)-1(2H)-pyridinyl]-butyl]-pyridine;
4-[3-(3,6-Dihydro-4-phenyl-1(2H)-pyridinyl)
4-[5-(3,6-Dihydro-4-phenyl pentyl]pyridine;
3-[4-(3,6-Dihydro-4-phenyl-1(2H)-pyridinyl)-butyl]-quinoline;
3-[4-[3,6-Dihydro-4-(2-pyridinyl)-1(2H)-pyridinyl]-butyl]quinoline;
2-[1,2,3,6-Tetrahydro-1-[4-(3-pyridinyl)butyl]-4-pyridinyl]pyridine;
4-(3,6-Dihydro-4-phenyl-1(2H)-pyridinyl)-1-(3-quinolinyl)-1-butanone;
3-[3-[3,6-Dihydro-4-(2-thienyl)-1(2H)-pyridinyl]-propyl]quinoline;
3-[3-(3,6-Dihydro-4-phenyl-1(2H)-pyridinyl)-propyl]-quinoline;
3-[5-[3,6-Dihydro-4-(2-thienyl)-1(2H)-pyridinyl]-butyl]-quinoline;
3-[5-(3,6-Dihydro-4-phenyl-1(2H)-pyridinyl)-pentyl]-quinoline; and
3-[5-(3,6-Dihydro-4-(2-thienyl)-1(2H)-pyridinyl]-pentyl]quinoline;
or a pharmaceutically acceptable acid addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, *Pharmacology, Biochemistry and Behavior*, Volume 8, pages 97–99 (1978); for their ability to inhibit [$^3$H]-spiroperidol binding in a receptor assay described by D. Grigoriadis and P. Seeman, *Journal of Neurochemistry*, Volume 44, pages 1925–1935 (1985); and for their ability to inhibit dopamine synthesis in rats according to the protocol described by J. R. Walters and R. H. Roth, *Naunyn-Schmiedebero's Archives of Pharmacology*, Volume 296, pages 5–14 (1976). The above test methods are incorporated herein by reference. The data in the table show the dopaminergic activity of representative compounds of Formula I.

TABLE 1

| | Biological Activity of Compounds of Formula 1 | | | |
|---|---|---|---|---|
| Example Number | Compound | Inhibition of Locomotor Activity in Mice ED$_{50}$, mg/kg, IP | % Reversal of Brain Dopamine Synthesis in Rats at 10 mg/kg, IP | Inhibition of [$^3$H]Spiroperido Binding IC$_{50}$, μM |
| 9 | 4-(3,6-Dihydro-4-phenyl-1-(2H)-pyridinyl)-1-(3-pyridinyl)-1-butanone | 1.1 | 50 | — |
| 12 | 3-[4-(3,6-Dihydro-4-phenyl-1(2H)-pyridinyl)butyl]pyridine | 0.28 | 80 | 0.17 |
| 8 | 3-[4-[3,6-Dihydro-4-(2-thienyl)-1(2H)-pyridinyl]butyl]butyl]pyridine | 0.66 | 71 | 1.29 |
| 10 | 4-(3,6-Dihydro-4-phenyl-1(2H)-pyridinyl)-1-(4-pyridinyl)- | 1.0 | 57 | 0.408 |

TABLE 1-continued

Biological Activity of Compounds of Formula 1

| Example Number | Compound | Inhibition of Locomotor Activity in Mice $ED_{50}$, mg/kg, IP | % Reversal of Brain Dopamine Synthesis in Rats at 10 mg/kg, IP | Inhibition of [$^3$H]Spiroperido Binding $IC_{50}$, μM |
|---|---|---|---|---|
| | 1-butanone | | | |
| 1 | 4-[4-(3,6-Dihydro-4-phenyl-1(2H)-pyridinyl)butyl]pyridine | 0.6 | 87 | 0.096 |
| 2 | 2-[1,2,3,6-Tetrahydro-1-[4-(4-pyridinyl)butyl]-4-pyridinyl]-pyridine | 0.7 | 88 | 0.448 |
| 3 | 3-[1,2,3,6-Tetrahydro-1-[4-(4-pyridinyl)butyl]pyridinyl]-1H-indole | 5.0 | — | 0.398 |
| 4 | 4-[4-[3,6-Dihydro-4-(2-thienyl)-1(2H)-pyridinyl]butyl]pyridine | 1.2 | — | 0.69 |
| 5 | 4-[3-(3,6-Dihydro-4-phenyl-1-(2H)-pyridinyl)propyl]pyridine | 0.63 | 61 | — |
| 7 | 4-[5-(3,6-Dihydro-4-phenyl-1(2H)-pyridinyl)pentyl]pyridine | 0.90 | — | — |
| 13 | 3-[4-(3,6-Dihydro-4-phenyl-1-(2H)-pyridinyl)butyl]quinoline | 0.37 | 100 | 0.046 |
| 15 | 3-[4-[3,6-Dihydro-4-(2-pyridinyl)]-1-(2H)-pyridinyl]butyl]quinoline | 0.14 | — | — |
| 14 | 3-[5-[3,6-Dihydro-4-(2-thienyl)]-1-(2H)-pyridinyl]butyl]quinoline | 1.50 | — | — |

A compound of Formula Ia

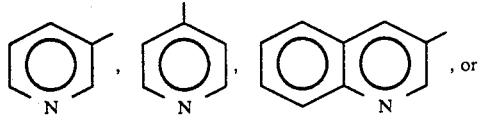

Ia wherein
R is

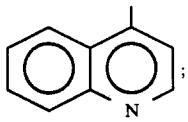, , 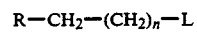, or

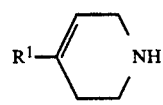;

n is an integer of 2 to 4;
R$^1$ is aryl, 2- or 3-1H-indolyl, or 2- or 3-1H indolyl substituted by lower alkyl, lower alkoxy, or halogen, 2-, 3-, or 4-pyridinyl, or 2-, 3-, or 4-pyridinyl substituted by lower alkyl, lower alkoxy, or halogen, 2-, 4-, or 5-pyrimidinyl, or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl, or 2- or 3-thienyl substituted by lower alkyl or halogen, 2- or 3-furanyl, or 2- or 3-furanyl substituted by lower alkyl or halogen, 2-, 4-, or 5-thiazolyl, or 2-, 4-, or 5 thiazolyl substituted by lower alkyl or halogen; or a pharmaceutically acceptable acid addition salt thereof may be prepared by reacting a compound of Formula Ib

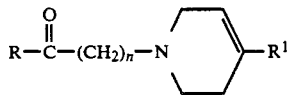

Ib wherein R, R$^1$, and n are as defined above with a reducing agent such as, for example, hydrazine, in the presence of an alkaline catalyst such as sodium hydroxide, potassium hydroxide, sodium methoxide, sodium ethoxide and the like, and a solvent such as, for example, ethylene glycol and the like, or amalgamated zinc and an acid such as, for example, concentrated hydrochloric acid and the like, optionally in the presence of a solvent such as, for example, ethanol, acetic acid, dioxane, toluene and the like, or treating a compound of Formula Ib with hydrogen in the presence of a catalyst such as a noble metal, for example, palladium on charcoal in the presence of a solvent such as, for example, ethanol and the like to give a compound of Formula Ia. Preferably, the reaction is carried out with hydrazine in the presence of potassium hydroxide and ethylene glycol.

Alternatively, a compound of Formula Ia may be prepared from a compound of Formula II $$R-CH_2-(CH_2)_n-L \qquad II$$

wherein L is a halogen, or a leaving group such as, for example, methanesulfonyloxy, toluenesulfonyloxy and the like, and R and n are as defined above, and a compound of Formula III

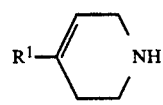

III wherein R$^1$ is as defined above in the presence of a base such as, for example, an alkali metal or alkaline earth metal hydroxide, carbonate or bicarbonate, for example, sodium hydroxide, sodium carbonate, sodium bicarbonate, potassium hydroxide, potassium carbonate, potassium bicarbonate and the like in the presence of a solvent such as, for example, acetonitrile and the like to give a compound of Formula Ia. Preferably, the reaction is carried out in the presence of potassium bicarbonate and acetonitrile.

A compound of Formula Ib is prepared from a compound of Formula IV

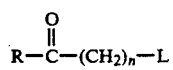

$$R-\overset{O}{\underset{\|}{C}}-(CH_2)_n-L \qquad IV$$

wherein R, N, and L are as defined above and a compound of Formula III using the methodology used to prepare a compound of Formula Ia from a compound of Formula II and a compound of Formula III.

Compounds of Formula II, Formula III, and Formula IV are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted foom 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

4-(3,6-Dihydro-4-phenyl-1(2H)-pyridinyl)butyl]-pyridine

A mixture of 4-(4-pyridinyl)-1-butylchloride (Example A) (0 76 g, 4.47 mmol), 1,2,3,6-tetrahydro-4-phenylpyridine (0.796 g, 5.0 mmol), and potassium bicarbonat (1.0 g, 10 mmol) in 5 mL of acetonitrile are heated to reflux for 8 hours. The reaction is cooled to room temperature and the acetonitrile removed in vacuo. The residue is partitioned between 50 mL of water and 50 mL of chloroform. The aqueous layer is extracted again with 50 mL of chloroform and the combined organic extracts are dried over sodium sulfate and the solvent removed in vacuo. The resulting residue is chromatographed on silica gel (2% to 3% methanol, 0.1% ammonia, chloroform) to obtain 1.10 g of 4-[4-(3,6-dihydro-4-phenyl-1(2H)-pyridinyl)-butyl]pyridine as a white solid; mp 89'

In a process analogous to Example 1 using appropriate starting materials, the corresponding compounds of Formula I (Examples 2 to 8) are prepared as follows:

EXAMPLE 2

[1,2,3,6-Tetrahydro-1-[4-(4-pyridinyl)butyl]-4-pyridinyl]pyridine; mp 98°-99° C.

EXAMPLE 3

3-[1,2,3,6-Tetrahydro-1-[4-(4-pyridinyl)butyl]-4-pyridinyl]]-1H-indole; mp 177

EXAMPLE 4

4-[4-[3,6-Dihydro-4-(2-thienyl)-1(2H)-pyridinyl]-butyl]-pyridine; mp 86°-87°

EXAMPLE 5

4-[3-(3,6-Dihydro-4-phenyl-1(2H)-pyridinyl)propyl]-pyridine; mp 166°-168° C.

EXAMPLE 6

2-[1,2,3,6-Tetrahydro-1-4-(3-pyridinyl)butyl}-4-pyridinyl]pyridine.

EXAMPLE 7

4-5-(3,6-Dihydro-4-phenyl-1(2H)-pyridinyl)butyl]-pyridine; mp 125°-126° C.

EXAMPLE 8

4-[3,6-Dihydro-4 (2-thienyl) 1{2H) pyridinyl]-butyl]pyridine; mp 44°-46° C.

EXAMPLE 9

4-(3,6-Dihydro-4-phenyl-1(2H)-pyridinyl)-1-(3-pyridinyl)-1-butanone

A solution of 4 chloro 3-(3-pyridinyl)-1-butanone (Example D) (17.8 g, 0.097 mol), 4-phenyl-1 2,3,6-tetrahydropyridine (44.7 g, 0.281 mol), an potassium iodide (0.8 g, 0.005 mol) are heated on a steam bath for 15 minutes. The residue is taken up in chloroform (60 mL) and the precipitate is filtered. The filtrate is evaporated in vacuo and purified by column chromatography (silica gel, 2% methanol/dichloromethane). The major product is crystallized from diethyl ether to give 4.5 g of 4-(3,6-dihydro-4-phenyl-1(2H)-pyridinyl)-1-(3-pyridinyl)-1-butanone as a solid; mp 64°-66° C.

In a process analogous to Example 9 using appropriate starting materials the corresponding compounds of Formula I (Examples 10 to 12) are prepared as follows:

EXAMPLE 10

4-(3,6-Dihydro-4-phenyl-1(2H)-pyridinyl)-1-(4-pyridinyl) 1-butanone; mp 97°-98° C.

EXAMPLE 11

4-(3,6-Dihydro-4-phenyl-1(2H)-pyridinyl)-1-(3-quinolinyl)-1-butanone; mp 106°-107° C.

EXAMPLE 12

3-4-(3,6-Dihydro-4-phenyl-1(2H)-pyridinyl)butyl]-pyridine; mp 45°-46° C.

EXAMPLE 13

3-[4-(3,6-Dihydro-4-phenyl-1(2H)-pyridinyl)butyl]-quinoline

A solution of 4-(3-quinolinyl)butan-1-ol (Example E) (2.0 g, 0.01 mol), N,N diisopropyl-ethylamine (3.5 mL, 0.02 mol) and a catalytic amount of 4-dimethylaminopyridine is cooled to 0° C and methanesulfonyl chloride (0.8 mL, 0.0105 mol) is added dropwise. The solution is stirred at 0° C. for 18 hours, and concentrated under reduced pressure. The residue is taken up in dimethylformamide (20 mL), and to this solution is added 4-phenyl-1,2,3,6-tetrahydropyridine (2.41 g, 0.015 mol) and sodium bicarbonate (3.4 g, 0.04 mol). The mixture is heated at 40° C. for 5 hours and the solvent removed under reduced pressure. The residue is partitioned between 50 mL of ethyl acetate and 50 mL of water. The aqueous layer is extracted with 50 mL of ethyl acetate and the organic extracts are dried (sodium sulfate) and the solvent removed in vacuo. The residue is chromatographed (silica gel, 2% methanol/98% dichloromethane) to give 2.15 g of the title compound; mp 92.8°-93.9° C.

In a process analogous to Example 13 using appropriate starting materials the corresponding compounds of Formula I (Examples 14 to 19) are prepared as follows:

EXAMPLE 14

3-[5-3,6-Dihydro 4-(2-thienyl-1(2H)-pyridinyl]-butyl quinoline; mp 73.8°–74.8° C.

EXAMPLE 15

3-4-[3,6-Dihydro-4 (2-pyridinyl)-1(2H)-pyridinyl -butyl]quinoline; mp 81.2°–81.6° C.

EXAMPLE 16

3-[3-[3,6-Dihydro-4-(2-thienyl)-1(2H)-pyridinyll- propyl]quinoline.

EXAMPLE 17

3-[3-(3,6-Dihydro 4 phenyl-1(2H]-pyridinyl)propyl]-quinoline dihydrochloride salt; mp 166°–67° C.

EXAMPLE 18

3-5-3,6-Dihydro-4-(2-thienyl)-1(2H)-pyridinyl -pentyl]quinoline.

EXAMPLE 19

3-[5-(3,6-Dihydro4-phenyl-1(2H)-pyridinyl)pentyl]- quinoline dihydrochloride salt; mp 162°–163° C.

PREPARATION OF STARTING MATERIALS

Example 4

4-(4-Pyridinyl)-1-butylchloride

A solution of 4-(4-pyridinyl)-1-butanol (Mayer J. M. and Testa, B., -Helv. Chim. Acta 65, pages 1868–1884 (1982) (4.20 g, 27.7 mmol) in 30 mL of chloroform is cooled to 0° C. and treated with thionyl chloride (6.60 g, 55.54 mmol) in 30 mL of chloroform. The reaction is allowed to warm to room temperature over 15 hours. The volatiles are removed in vacuo. The residue is cooled to 0° C. and treated with 50 mL of cold 10% sodium hydroxide solution and the mixture is extracted with three 100-mL portions of chloroform. The combined organic extracts are dried over sodium sulfate and the solvents are removed under reduced pressure to give 4.25 g of 4-(4-pyridinyl)-1-butylchloride as a brown oil.

In a process analogous to Example A using appropriate starting materials the corresponding compound was prepared as follows:

Example B 3-(4-Pyridinyl)-propylchloride (Mayer, J. M. and Testa, B., Helv. Chim. Acta, pages 1868–1884 (1982)).

Example C 5-(4-Pyridinyl)-pentylchloride

Step

A: Preparation of 4-(Chlorobutoxy)-3,4,5,6-2H-tetrahydropyran

A solution of 4-chlorobutanol (23.2 g, 0.2140 mol) and 2 drops of concentrated hydrochloric acid at 0° C. is treated with 3,4-dihydro-2H-pyran (15 g, 0.1 783 mol). The reaction is allowed to warm to room temperature over 3 hours. The reaction mixture is purified by distillation (130° C., 20 mm) to give 18.07 g of 2-(4-chlorobutoxy)-3,4,5,6-2H-tetrahydropyran as a colorless oil.

Step B

Preparation of 5-(4-Pyridinyl)-1-pentanol

Phenyl lithium (1.8 M cyclohexane diethyl ether, 27.6 mL, 0.0497 mol) is slowly added to a stirring solution of 4-picoline (4.6 g, 0.0497 mol) in 50 mL of tetrahydrofuran under nitrogen. The solution is stirred for 20 minutes at room temperature and then cooled to 0° C. 2-(4 Chlorobutoxy)-3,4,5,6-2H-tetrahydropyran (6.4 g, 0.0332 mol) is slowly adde to the reaction mixture and the mixture is stirred for 30 minutes at 0° C. The reaction mixture is refluxed for 12 hours, cooled, and 100 mL of 10% hydrochloric acid solution is added. The reaction mixture is stirred for another 12 hours and then made basic with a saturated solution of sodium bicarbonate and extracted with chloroform. The organic phase is dried (sodium sulfate) and evaporated in vacuo. The resulting residue is chromatographed on silica gel (ethyl acetate) to give 1.25 g of 5-(4-pyridinyl)-1 pentanol as a brown oil.

Step C

Preparation of 5-(4-Pyridinyl)-1-pentyl-chloride

A solution of 5-(4-pyridinyl)-l-pentanol (3.71 g, 0.0225 mol) in 50 mL of chloroform is treated with thionyl chloride (5.4 g, 0.0449 mol) in 25 mL of chloroform. The resulting solution is neutralized with a saturated solution of sodium bicarbonate and extracted with chloroform. The organic phase is dried (sodium sulfate) and evaporated in vacuo to give 3.86 g of 5-(4-pyridinyl)-1-pentylchloride as a brown oil.

Example D

4-Chloro-1-(3-pyridinyl)-1-butanone (Sato, M., et al, Chem. Pharm. Bull., 26, 3296 (1978))..

A solution of methyl nicotinate (59 g, 0.43 mol), 4 hydroxybutyric acid lactone (51.8 g, 0.602 mol), and sodium methoxide (70 g, 1.29 mol) in dioxane (500 mL) is refluxed for 1 hour and then cooled. Concentrated hydrochloric acid (650 mL) is added, and the reaction mixture is refluxed for 12 hours. The resulting solution is neutralized with solid sodium bicarbonate and extracted with chloroform. The organic phase is dried (sodium sulfate), and the solvent evaporated in vacuo. The residue is taken up in 2-propanol (50 mL) and treated with a saturated solution of hydrogen chloride in 2-propanol. The hydrochloride salt of 4 chloro-1-(3-pyridinyl)-1-butanone is obtained as a white solid (30 g); mp 73°–76° C.

Example E 4-(3 Quinolinyl)butan-1-ol

Step A

Preparation of 4-(3-Quinolinyl) 3-butyn-1-ol

· A solution of 3-bromoquinoline (13.57 mL, 0.10 mol) and 3-butyn-1 ol (9.0 mL, 0.12 mol) in 40 mL of triethylamine and 75 mL of dichloromethane is degassed by bubbling dry nitrogen through it for 15 minutes, and 0.7 g (0.00I mol) of bis(triphenyl-phosphine)palladium dichloride and 0.013 g of cuprous iodide are added. The flask is flushed with nitrogen and the mixture heated to reflux for 5 hours. The cooled mixture is diluted with dichloromethane and washed with water, dried (sodium sulfate), and concentrated to give 27 g of a gold oil. The oil was triturated with diethyl ether to give 18.2 g of the title compound as a tan solid; mp 95.7°–96.7° C.

Step B

Preparation of 4-(3-Quinolinyl)butan-1-ol

A solution of 4-(3-quinolinyl)-3-butyn-1-ol (17.0 g, 0.086 mol) is hydrogenated over palladium on carbon (1.0 g) in ethanol (400 mL) at room temperature. After the catalyst is filtered, the solvent is removed under reduced pressure to give 17.3 g of a brown oil. The oil is chromatographed (silica gel, 2% methanol/98% dichloromethane) to give 13.5 g of the title compound as a yellow oil.

We claim:

1. A compound of Formula I

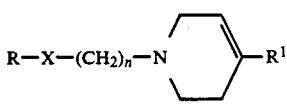

wherein
$R^1$ is

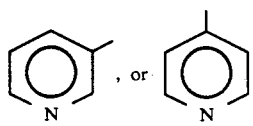

X is

or —CH$_2$—;

n is an integer of 2 to 4 with the proviso that when X is —CH$_2$—, n is 3 or 4;
$R^1$ is 2- or 3-1H-indilyl, or 2- or 3-1H-indolyl substituted by lower alkyl, lower alkoxy, or halogen, 2-, 3-, or 4-pyridinyl, or 2-, 3-, or 4-pyiridinyl substituted by lower alkyl, lower alkoxy, or halogen, 2- or 3-furanyl, or 2-or 3-furanyl substitued by lower alkyl or halogen, 2-, 4-, or 5-thiazolyl, or 2-, 4-, or 5- thiazoyl substituted by lower alkyl or halogen; or a pharmaceutically acceptable acid addition salt thereof.

2. A compound according to claim 1, in which $R^1$ is 2-or 3-1H-indolyl, or 2- or 3-1H-indolyl substituted by lower alkyl, lower alkoxy, or halogen, 2-, 3-, or 4-pyridinyl, or 2-, 3-, or 4-pyridinyl substituted by lower alkyl, lower alkoxy, or halogen[2-, 4-, or 5-pyrimidinyl, or 2-, 4-, or 5-pyrimidinyl substituted by lower alkyl, lower alkoxy, or halogen, 2- or 3-thienyl or 2- or 3-, thienyl substituted by lower alkyl or halogen.].

3. A compound according to claim 2, in which $R^1$ is [aryl,]2-or 3-1H-indolyl, 2-, 3-, or 4-pyridinyl,[2-, 4-, or 5-pyrimidinyl, or 2- or 3-thienyl].

4. A method of treating schizophrenia comprising administering to a host suffering therefrom a therapeutic effective amount of a compound according to claim 1 in unit dosage form.

5. A method of treating depression comprising administering to a host suffering therefrom a therapeutic effective amount of a compound according to claim 1 in unit dosage form.

6. A compound according to claim 3 selected from the group consisting of:
2-[1,2,3,6-Tetrahydro-1-[4-(4-pyridinyl) butyl]-4-pyridinyl]pyridine;
3-[1,2,3,6-Tetrahydro1-[4-(4-pyridinyl)butyl]-4-pyridinyl]-1H-indole; and
2-[1,2,3,6-Tetrahydro-1-[4-(3-pyridinyl)-butyl]-4-pyridinyl]pyridine.

* * * * *

UNITED STATES PATENT AND TRADEMARK OFFICE
CERTIFICATE OF CORRECTION

PATENT NO. : 5,187,280  
DATED : FEBRUARY 16, 1993  
INVENTOR(S) : JUAN JAEN, DAVID NICKELL, DONNA REYNOLDS, SARAH SMITH, L. D. WISE, D. J. WUSTROW

Page 1 of 2

It is certified that error appears in the above-indentified patent and that said Letters Patent is hereby corrected as shown below:

COLUMN 14, line 3,
        delete "indilyl"
        insert --indolyl-- lines 16-19,
        delete "[2-, 4-, or 5-pyrimidinyl, or 2-, 4-, or 5-pyrimidinyl substituted by lower alkyl, lower alkoxy, or halogen, 2- or 3-thienyl or 2-, or 3-, thienyl substituted by lower alkyl or halogen.]"

line 21,
        delete "[aryl,]"

lines 21-22,
        delete ",[2-, 4-, or 5-pyrimidinyl, or 2- or 3-thienyl]"

UNITED STATES PATENT AND TRADEMARK OFFICE
CERTIFICATE OF CORRECTION

PATENT NO. : 5,187,280
DATED : FEBRUARY 16, 1993
INVENTOR(S) : JUAN JAEN, DAVID NICKELL, DONNA REYNOLDS
SARAH SMITH, L. D. WISE, D. J. WUSTROW

It is certified that error appears in the above-indentified patent and that said Letters Patent is hereby corrected as shown below:

COLUMN 14, line 35,
        delete "Tetrahydrol-"
        insert --Tetrahydro-1- --

Signed and Sealed this

Twenty-third Day of November, 1993

Attest:

BRUCE LEHMAN

*Attesting Officer*      *Commissioner of Patents and Trademarks*